US00PP13768P29

(12) United States Plant Patent
Kolster

(10) Patent No.: US PP13,768 P2
(45) Date of Patent: May 6, 2003

(54) ILEX PLANT NAMED 'KOLMBER'

(75) Inventor: Peter R. Kolster, Boskoop (NL)

(73) Assignee: Gebr. Kolster BV, Boskoop (NL)

( * ) Notice: Subject to any disclaimer, the term of this patent is extended or adjusted under 35 U.S.C. 154(b) by 0 days.

(21) Appl. No.: 10/159,061

(22) Filed: May 31, 2002

(51) Int. Cl.[7] ..... A01H 5/00
(52) U.S. Cl. ..... Plt./247
(58) Field of Search ..... Plt./247

(56) References Cited

U.S. PATENT DOCUMENTS

RE29,912 E * 2/1979 Simpson ..... Plt./247

OTHER PUBLICATIONS

UPOV ROM GTITM Computer Database, GTI JOUVE software 2002/02, citations(s) for 'Kolmber'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Ilex plant named 'Kolmber', characterized by its upright plant habit; freely branching growth habit; freely flowering habit; and numerous orange red-colored drupes.

1 Drawing Sheet

BOTANICAL CLASSIFICATION/CULTIVAR DESIGNATION

*Ilex verticillata* cultivar Kolmber.

BACKGROUND OF THE INVENTION

The present Invention relates to a new and distinct cultivar of Ilex plant, botanically known as *Ilex verticillata*, and hereinafter referred to by the name 'Kolmber'.

The new Ilex was discovered as a cross-pollination of two unidentified selections of *Ilex verticillata*, not patented. The new Ilex was discovered and selected by the Inventor in 1997 as a single flowering plant in a controlled environment in Boskoop, The Netherlands, within a population of the progeny resulting from the cross-pollination.

Asexual reproduction of the new Ilex by cuttings was first conducted in Boskoop, The Netherlands in 1997. Since then, asexual reproduction by cuttings has shown that the unique features of this new Ilex are stable and reproduced true to type in successive generations.

SUMMARY OF THE INVENTION

The cultivar Kolmber has not been observed under all possible environmental conditions. The phenotype may vary somewhat with variations in environment such as temperature and light intensity without, however, any variance in genotype.

The following traits have been repeatedly observed and are determined to be the unique characteristics of 'Kolmber'. These characteristics in combination distinguish 'Kolmber' as a new and distinct Ilex:

1. Upright plant habit.
2. Freely branching growth habit.
3. Freely flowering habit.
4. Numerous orange red-colored drupes.

Plants of the new Ilex differ primarily from plants of the parent selections and other known selections and cultivars of *Ilex verticillata* primarily in growth habit.

BRIEF DESCRIPTION OF THE PHOTOGRAPH

The accompanying colored photograph illustrates the overall appearance of the new Ilex showing the colors as true as it is reasonably possible to obtain in colored reproductions of this type. Colors in the photograph may differ from the color values cited in the detailed botanical description which accurately describe the colors of the new Ilex. The photograph comprises a side perspective view of a typical flowering plant of 'Kolmber' grown in an outdoor nursery in Boskoop, The Netherlands.

DETAILED BOTANICAL DESCRIPTION

The aforementioned photographs and following observations and measurements describe plants grown in Boskoop, The Netherlands, in an outdoor nursery under full sun conditions. The photographs and the observations and measurements were taken during the summer of 2001; plants used for the photographs, observations and measurements were about three years old. During the summer, day temperatures ranged from 14 to 20° C. and night temperatures ranged from 7 to 12° C. Color references are made to The Royal Horticultural Society Colour Chart, 2001 edition, except where general terms of ordinary dictionary significance are used.

Botanical classification: *Ilex verticillata* cultivar Kolmber.
Parentage:
*Female, or seed, parent.*—Unidentified selection of *Ilex verticillata*, not patented.
*Male, or pollen, parent.*—Unidentified selection of *Ilex verticillata*, not patented.
Propagation:
*Type.*—By cuttings.

*Time to initiate roots.*—About 40 days at 18° C.

*Time to produce a rooted plant.*—About 90 days at 18° C.

*Root description.*—Fine, freely branching.

Plant description:

*Appearance.*—Perennial woody shrub. Upright plant habit; broad columnar plant shape. Very freely branching; about 20 lateral branches develop per plant; dense and full plants. Moderately vigorous growth habit.

*Plant height.*—About 150 cm.

*Plant width or area of spread.*—About 80 cm.

*Lateral branches.*—Length: About 13 cm. Diameter: About 2 mm. Internode length: About 1.5 cm. Strength: Strong. Texture: Smooth, glabrous. Color, immature: 138A. Color, mature: 198A. Lenticels: Length: About 1 mm. Diameter: About 1.2 mm. Color: 199C to 199D.

*Foliage description.*—Arrangement: Alternate; single. Length: About 6.2 cm. Width: About 2.6 cm. Shape: Elliptic. Apex: Apiculate. Base: Attenuate. Margin: Serrulate. Venation pattern: Pinnate. Texture, upper surface: Smooth, glabrous; slightly rugose. Texture, lower surface: Pubescent on primary veins; slightly rugose. Color: Young foliage, upper surface: 137A. Young foliage, lower surface: 144A. Fully expanded foliage, upper surface: 137A. Fully expanded foliage, lower surface: 143A. Venation, upper surface: 137A. Venation, lower surface: 145C; young leaves, overlain with close to 59A. Petiole: Length: About 1 cm. Diameter: About 1 mm. Texture, upper and lower surfaces: Glabrous. Color, upper and lower surfaces: 145C; young leaves, overlain with close to 59A.

Flower description:

*Appearance.*—Small axillary cup-shaped flowers; solitary or in clusters of two or three. Flowers face upright to outward. Flowers not persistent.

*Flowering response.*—Plants flower continuous and freely during the summer, typically during July in Boskoop, The Netherlands. Postproduction longevity: Individual flowers maintain good color and substance for about two or three days on the plant when grown in an outdoor environment.

*Quantity of flowers.*—Freely flowering; about 72 open flowers and flower buds per lateral stem per flowering season.

*Fragrance.*—None detected.

*Flower bud.*—Length: About 2 mm. Diameter: About 2 mm. Shape: Globular. Color: 157A.

*Flower diameter.*—About 5 mm.

*Flower height* (*depth*).—About 2.5 mm.

*Petals.*—Quantity per flower: Seven. Length: About 3 mm. Width: About 1.5 mm. Shape: Oblong. Apex: Rounded. Base: Attenuate. Margin: Entire. Texture, upper and lower surfaces: Smooth, glabrous. Color: Developing and fully expanded petals, upper surface: 157B. Developing and fully expanded petals, lower surface: 157A.

*Sepals.*—Quantity per flower: Seven. Length: About 1.5 mm. Width: About 1 mm. Shape: Deltoid. Apex: Acute. Base: Fused. Margin: Entire. Texture, upper and lower surfaces: Smooth, glabrous. Color: Developing and fully expanded sepals, upper surface: 144A to 144B. Developing and fully expanded sepals, lower surface: 144A to 144B.

*Peduncles.*—Length: About 2.5 mm. Diameter: About 0.8 mm. Orientation: About 20 to 40° from vertical. Strength: Strong. Color: 144A to 144B.

*Reproductive organs.*—Stamens: Quantity per flower: About seven. Anther shape: Narrowly deltoid; basifixed. Anther length: About 0.8 mm. Anther color: 157D. Pollen amount: None observed. Pistils: Quantity per flower: One. Pistil length: About 5 mm. Stigma shape: Oblong, flattened. Stigma color: 144A. Ovary color: 143A.

*Fruits.*—Quantity per flower: One. Days to ripening: About 75. Longevity on the plant: More than two weeks. Type: Drupe. Length: About 7 mm. Diameter: About 8 mm. Shape: Spherical. Texture: Smooth, glabrous. Color: N34A to 45A.

*Seeds.*—Quantity per fruit: About seven. Length: About 5 mm. Diameter: About 3 mm. Texture: Smooth, glabrous. Color: 152C.

Disease resistance: Plants of the new Ilex have not been observed to be resistant to pathogens common to Ilex.

Temperature tolerance: Plants of the new Ilex have been observed to tolerate temperatures from about −25 to 39° C.

It is claimed:

1. A new and distinct cultivar of Ilex plant named 'Kolmber', as illustrated and described.

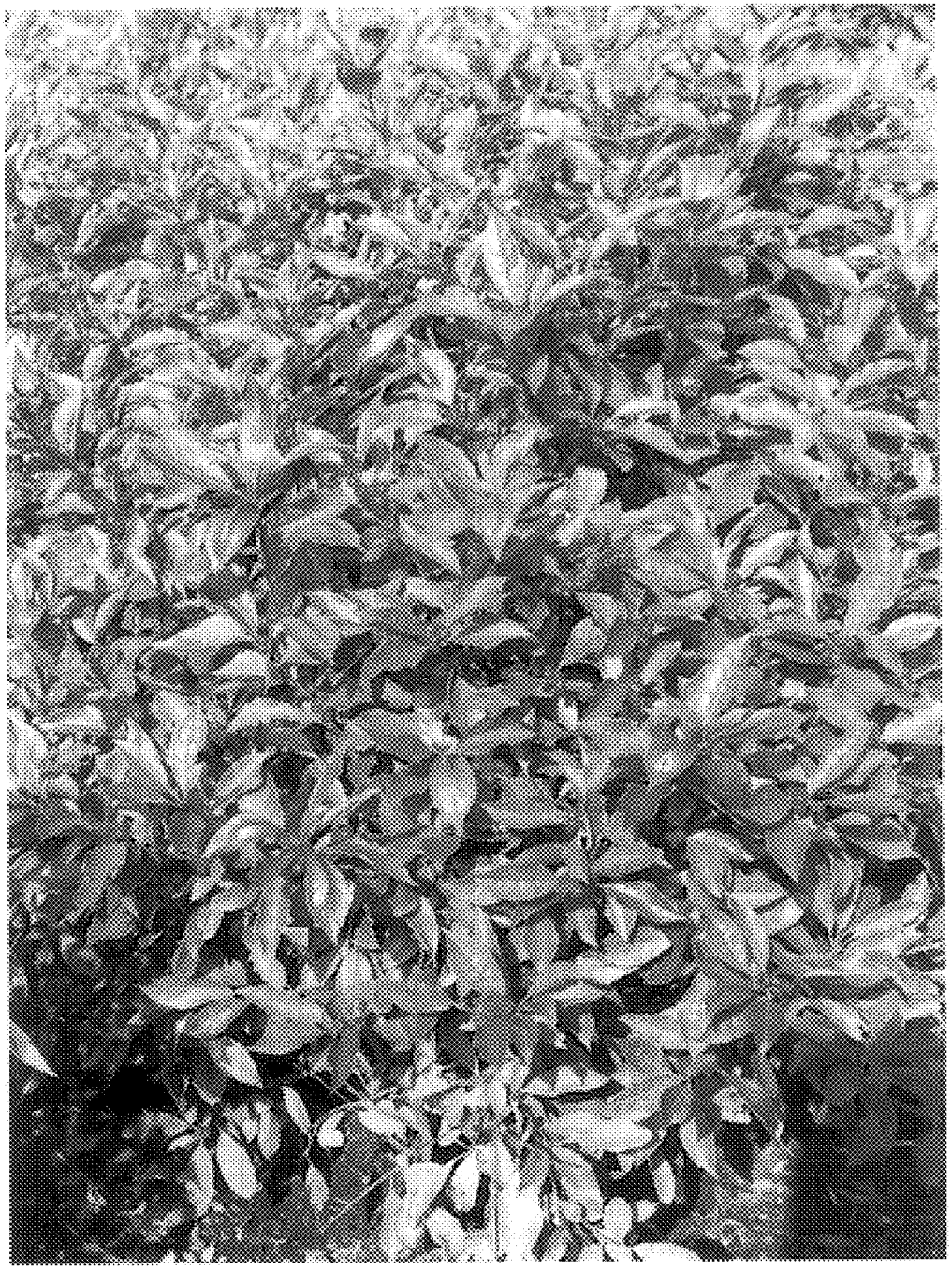

* * * * *